United States Patent [19]

Reichstein

[11] Patent Number: 4,632,119
[45] Date of Patent: Dec. 30, 1986

[54] AMBULATORY ESOPHAGEAL PH MONITOR

[75] Inventor: Benjamin J. Reichstein, Wilmette, Ill.

[73] Assignee: University of Health Sciences/The Chicago Medical School, North Chicago, Ill.

[21] Appl. No.: 790,359

[22] Filed: Oct. 23, 1985

[51] Int. Cl.$^4$ .............................................. A61B 5/00
[52] U.S. Cl. .................................. 128/632; 128/636; 436/163
[58] Field of Search ............... 128/630, 632, 636, 638, 128/670, 759; 436/163, 178

[56] References Cited

U.S. PATENT DOCUMENTS

| | | | |
|---|---|---|---|
| 2,664,879 | 9/1950 | Hardy | 128/636 |
| 3,097,636 | 5/1961 | Haynes, Jr. et al. | 128/638 |
| 3,373,735 | 3/1968 | Gallagher | 128/2 |
| 3,483,859 | 11/1967 | Pittman | 128/638 |
| 3,528,429 | 9/1970 | Beal | 128/2 |
| 4,029,598 | 6/1977 | Neisius et al. | 436/163 |
| 4,200,110 | 4/1980 | Peterson et al. | 128/636 |
| 4,381,011 | 4/1983 | Somers | 128/635 |

OTHER PUBLICATIONS

"A Clinical Evaluation of Tubeless Gastric Analysis", by R. J. Bolt et al., Gastroenterology, vol. 32, Jan. 1957, pp. 34–41.
Chang, et al., An Improved Technic for Tubeless Gastric Analysis, Am J Gastroent, 42:165, (1964).
Segal, et al., Tubeless Gastric Analysis with an Azure A Ion-Exchange Compound, Gastroenterology, 28:402, (1955).
Vantrappen, et al., Twenty-Four Hour Esophageal pH and Pressure Recording in Outpatients, Motility of the Digestive Tract, M. Wienbeck (ed.), Raven Press, New York, 1982.
Segal, et al., Determination of Gastric Acidity without Intubation . . . Proc Soc Exp Biol Med, 74: 218, 1950.
Fink, et al., The Role of Prolonged Esophageal pH Monitoring . . . Journal of the American Medical Association, 1984.
Imcomed brochure, Spectacular Progress in Diagnosis of Esophageal Disorders, Imcomed, Aarschotsestraat, 45–47, B–1801 Peutie, Vilvoorde, Belgium.
Proxima 1, Proxima 2, Gastro Oesophageal pH Computer/Monitors, American Endoscopy, Inc., 9350 Progress Parkway, Mentor, Ohio 44060.
Sandhill Product Brochure, Ambulatory Reflex Monitor Model RMS, Sandhill, 1501 West Campus Drive, Unit N, Littleton, Colo. 80120.
Biosearch Medical Products, Inc. brochure, The Ambulatory Esophageal pH Monitor that Makes Medical History Every 24 Hours, 35 Industrial Parkway, P.O. Box 1700, Somerville, N.J. 08876.

Primary Examiner—Kyle L. Howell
Assistant Examiner—Randy Citrin
Attorney, Agent, or Firm—Wallenstein, Wagner, Hattis, Strampel & Aubel, Ltd.

[57] ABSTRACT

A unique ingestible and retrievable ambulatory esophageal monitor for colorimetric analysis of ambient pH within selected portions of the esophagus comprising a nasoesophgeal conduit at least one generally transparent semi-permeable envelope carried proximal the distal end of the conduit for positioning within the distal esophagus. The envelope contains an ion exchange color indicator composition comprised of a weak cation exchange substance selected from the group comprising a resin, a cellulose or an agarose and intermixed and bound therein being an indicator dye preferably either methylene blue or azure A. The ion exchange substance having a disassociation potential (pK) of at least 4 so that the indicator dye selectively disassociates causing the envelope to visually discolorize when exposed to a clinically significant ambient pH of 4 or less within the esophagus.

7 Claims, 7 Drawing Figures

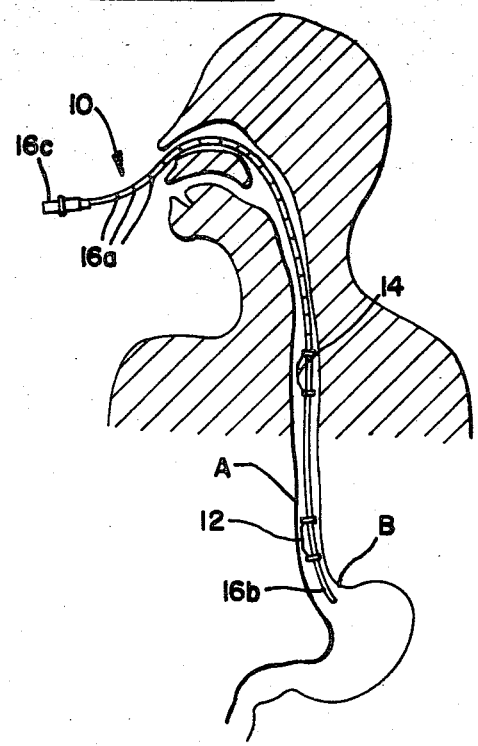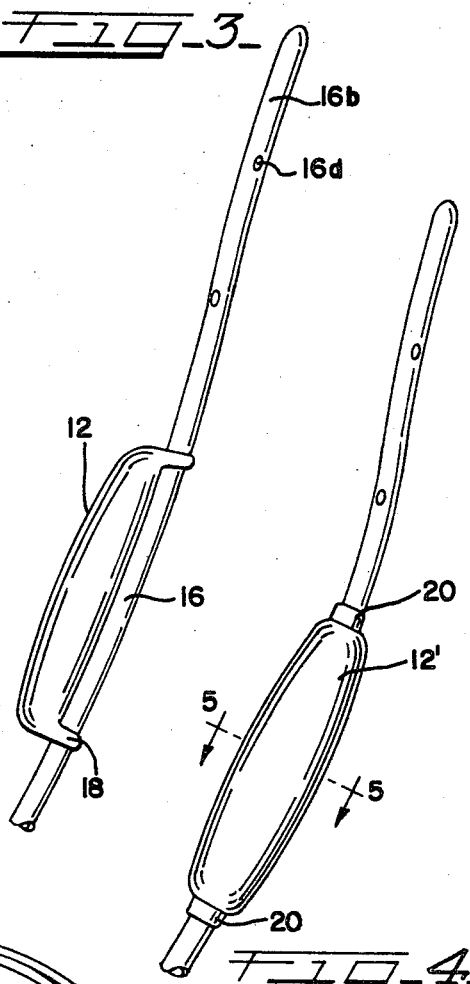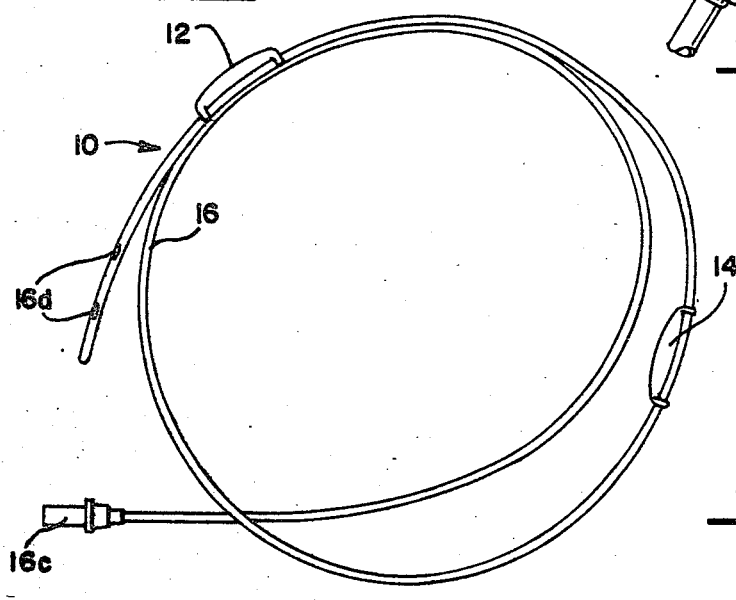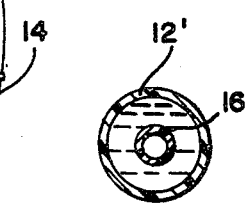

AMBULATORY ESOPHAGEAL PH MONITOR

DESCRIPTION

1. Technical Field

The present invention generally relates to apparatuses and methods for physiologic testing of the human gastrointestinal tract and, in particular, to an ambulatory esophageal pH monitor for colorimetric analysis of ambient pH within proximal portions of the esophagus such as the gastroesophageal junction.

2. Background of the Invention

The pH in the lumen of the distal esophagus does not remain constant. Periodically, reflux of gastric fluids from the stomach occurs causing a sudden decrease in pH within the esophagus to a highly acidic pH of less than 2. Such reflux of gastric fluids causes most pronounced changes of pH in the distal portion of the esophagus. The normal response of the esophagus is to reflexly initiate peristaltic contractions which propel refluxed gastric acid from the distal esophagus to the stomach. These contractions restore esophageal pH to physiologic neutrality.

Gastroesophageal reflux is a clinical disorder in which there may be excessive volumes of refluxed gastric fluid, abnormal frequency of reflux episodes or ineffective esophageal peristalsis. Any of such conditions exposes the tissues of the lower esophagus to prolonged periods of low pH. Severe acid reflux may cause erosion, ulceration, and bleeding from the esohagus. Repetitive episodes of acid reflux may produce stricture and shortening of the esophagus. In some individuals repetitive episodes of reflux may lead to an alteration of the surface layer of the esophagus termed Barrett's esophagus which may be a premalignant condition. Exposure of the distal esophagus to a pH of 4 or lower for a total period of time of 3 hours or more during a 24 hour period defines clinically significant gastroesophageal reflux disease. See, e.g. S. M. Fink & R. W. McCallum, The Role of Prolonged Esophageal pH Monitoring and the Diagnosis of Gastroesophageal Reflux, *Journal of the American Medical Association,* 1984; vol. 252, pp. 1160-1164.

Determination of the presence and amount of gastric acid refluxed into the distal esophagus may permit the identification of individuals who are at high risk for the development of these complications and who might be recommended medical or surgical treatment for this condition. The determination of acid reflux is also important in differentiating between cardiac and esophageal disease in individuals who manifest certain types of unusual chest pain. Finally, determination of the quantitative aspects of acid reflux may be helpful in following the course of patients who have been treated for esophageal reflux disease to assess the efficacy of their therapy.

However, esophageal pH testing is made difficult because esophageal pH, at any moment in time in a patient with significant reflux disease, is likely to reveal a normal pH. Episodes of reflux and peristaltic clearing occur only sporadically. In fact reflux episodes may be present only 15% of a 24 hour time period in patients with severe gastroesophageal reflux disease. Further, single moment measurement of the esophageal pH does not permit any assessment of the total time of esophageal tissue exposure to low pH.

The prior art suggests several technics of esophageal pH testing including intubated gastric analysis, tubeless gastric analysis and 24 hour electronic pH monitoring. Intubated gastric analysis consists of intubating a patient with a nasogastric tube and aspirating gastric secretions for in vitro analysis. An adjunct to intubation gastric analysis is the use of catheters or ingestible capsules containing an acid-base indicator as suggested in U.S. Pat. Nos. 3,373,735 and 3,528,429. However, intubated gastric analysis must be conducted within a hospital or other clinical setting. Moreover, this technic is labor intensive and therefore costly and does not determine duration of tissue exposure to clinically significant levels of low pH.

Tubeless gastric analysis is comprised of the patient ingesting a carboxylic cation resin, such as Diagnex Blue (Squibb) which has been combined with an indicator dye such as azure A. In the presence of a gastric pH below 3.5, the indicator dye is liberated from the cation exchange resin permitting the dye to be absorbed by the intestinal tissue and ultimately secreted into the urine. Periodic urine samples are then taken to detect for the presence of the dye in the urine. See, e.g. Chang, et al., An Improved Technic for Tubeless Gastric Analysis, *American Journal of Gastroenterology,* 1964; vol. 42 pp 165-171. Tubeless gastric analysis method is principally useful for patients who should not or cannot be intubated. Though tubeless gastric analysis is an extremely simple procedure, it is generally only considered as a measurement of gastric acid production and not as a test to determine exposure of esophageal tissue to repeated episodes of low pH thereby confirming or rejecting a clinical diagnosis of reflux disease.

More recently, the art has suggested use of electronic pH monitoring of the lower esophagus utilizing a suitable pH probe introduced orally or nasally to a position in the the distal esophagus such as disclosed in U.S. Pat. No. 4,381,011. The pH probe is connected via a lead wire to a chart recorder, and esophageal pH is continuously recorded for an extended period of time, usually 24 hours. Alternatively, the pH probe is connected to a portable, battery operated recorder which is carried in a holster and worn by the patient on an ambulatory basis. After the 24 hour time period, the probe is removed and the data which has been stored in the recorder is analyzed by computer. Examples of commercial embodiments of electronic pH monitoring devices included the Ambulatory Reflux Monitor by Sandhill; the Proxima ½ monitor by American Endoscopy, Inc.; and the Ambi-24 monitor by Biosearch Medical Products, Inc.

The former method requires that the patient be hospitalized for a 24 hour period. In addition, the patient is tethered to the pH recorder by the pH probe wire. This method is costly, cumbersome, and potentially misleading, since the patient's activities are greatly restricted by hospitalization and by the tethering pH probe wire. The second method permits ambulatory measurements; however, the patient is still required to wear a holster containing the recorder. In addition, both methods utilize non-disposable pH probes, a factor which increases expense, increases risk for transmission of infection, and requires complex sterilization procedures between uses.

Furthermore, electronic pH monitoring requires computer hardware and software for analysis of data stored on the chart recorder or holster recorder. The costs involved in electronic pH monitoring generally place this procedure out of reach for practicing internists and many consulting gastroenterologists. As a result, 24 hour monitoring has been generally restricted to major hospitals and research teaching centers.

Hence, prior to the present invention, a need existed for an inexpensive, disposable and easy to use ambulatory esophageal pH monitor permitting a determination of the duration of exposure of esophageal tissue to a clinically significant pH of 4 or less over a specified time period at a particular, known, position within the lumen of the distal esophagus.

SUMMARY OF THE INVENTION

According to the present invention, an ambulatory esophageal pH monitor has been developed generally encompassing at least one ingestible but retrievable semi-permeable envelope carried on a distal portion of a nasogastric conduit in which the envelope contains an ion exchange color indicator composition which discolorizes when exposed, over a selected time period, to acidic pH conditions. The envelope substantially discolorizes when exposed to clinically significant conditions of pH 4 or less. Unlike the prior art tubeless and intubated gastric analysis technics the present invention permits analysis of a specific site of gastric fluid reflux within the distal esophagus. Moreover, the monitor of the present invention permits a patient to remain ambulatory and therefore can be used on an out-patient basis thereby avoiding the artificial living conditons of a clinical environment. In addition, the monitor of the present invention is disposable and provides a semi-quantitative measure of total length of time in which esophageal tissue has been exposed to clinically significant pH conditions. Because the monitor of the present invention is inexpensive, it provides an opportunity for initial screening of patients "at-risk" to reflux disease during office visits thereby avoiding an expensive in-patient clinical work-up.

Generally, the esophageal pH monitor of the present invention includes a nasoesophageal conduit, preferably a probe or catheter, of a selected length so that a distal end of the catheter is approximately positioned 5 cm proximal to the gastroesophageal junction. Carried near a distal end of the catheter is a generally transparent semi-permeable envelope containing an ion exchanger color indicator composition. The composition elutes an indicator dye when exposed to an acidic ambient pH and becomes substantially discolorable at a pH of 4 or less. In the preferred embodiment of the present invention, a second control envelope is positioned proximal to the first envelope. The present ambulatory esophageal pH monitor further includes a means for maintaining the stationary positioning of each envelope along the conduit.

The ion exchange color indicator composition is comprised of a weak cation exchange substance selected from the group consisting of a resin, a cellulose and an agarose. Intermixed and bound within the ion exchange substance is an indicator dye preferably either methylene blue or azure A. Preferably, the ion exchange substance carries a disassociation value ("pK") of from 4 to 5 so that at a clinically significant pH of 4 or less, the indicator dye has disassociated from 90% of the available anionic bonding sites resulting in substantial discoloration of the ion exchange color indicator composition. As a result of such disassociation, the brightly colored generally transparent semi-permeable envelope visually appears paled and discolored in response to acidic ambient pH. The degree or percent of dye elution can be colorimetrically analyzed with a color indicating rule containing a continuum of colored panels to indicate, on a semi-quantitative basis, the length of time of exposure of esophageal tissue to gastric reflux fluids. Such data can either confirm or deny an initial diagnosis of a patient at risk to gastroesophageal reflux disease.

Other features and advantages of the present invention will become apparent from the following detailed description with reference to the drawings as well as the claims appended hereto.

BRIEF DESCRIPTION OF THE DRAWINGS

FIG. 1 is a perspective view illustrating intubation of the ambulatory esophageal pH of the present invention;

FIG. 2 is a plan view of one embodiment of the present invention;

FIG. 3 is a detailed perspective view of a distal end of the embodiment of the present invention disclosed in FIG. 2;

FIG. 4 is a detailed perspective view of another embodiment of the present invention;

FIG. 5 is a transverse sectional view taken along line 5—5 of FIG. 4;

DETAILED DESCRIPTION

Figure 6:
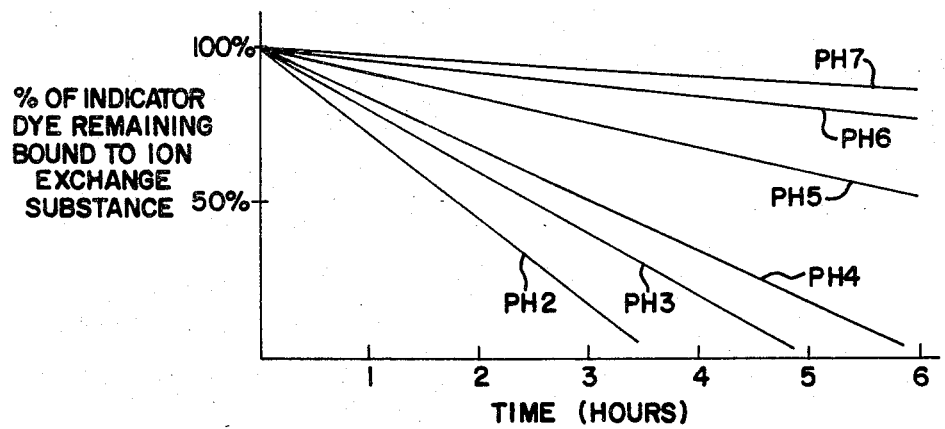
FIG. 6 is a graph disclosing preferred performance of the ion exchange color indicator composition; and, FIG. 7 is a perspective view of one embodiment of a colorimetric analysis rule of the present invention.

Referring now to the drawings, FIG. 1 discloses nasal intubation of one embodiment of an ambulatory esophageal pH monitor 10 of the present invention. Such intubation of pH monitor 10 positioning of an indicator envelope 12 within the distal esophagus A proximal or cephalad to gastroesophageal junction B. A second indicator envelope 14 is positioned within the intermediate esophagus such that envelope 14 may act as a control. Envelope 12 is preferably positioned about 5 centimeters above gastroesophageal junction B. In most adults gastroesophageal junction B occurs at a position 40 centimeters from the nares. As disclosed in FIG. 1, control envelope 14 is preferably positioned in the middle esophagus about 25 centimeters from envelope 12.

As disclosed in FIG. 1, envelopes 12 and 14 are carried on an esophageal conduit 16 preferably either a pliable probe or a nasoesophageal catheter. Conduit 16 must be chemically inert, biocompatible, and unstainable by non-toxic dyes. Esophageal conduit 16 contains length calibrations 16a which are utilized for intubation and selective positioning of envelope 12 proximal to gastroesophageal junction B. Calibrations 16a are preferably marked in one centimeter increments utilizing a water insoluble non-toxic dye. In addition, esophageal conduit 16 preferably includes a tungsten weighted distal end 16b to assist in intubation. Where conduit 16 embodies a nasoesophageal catheter or enteral feeding tube as disclosed in FIGS. 1 and 2, a luer end 16c is carried on the proximal end to permit usage of an intubation stylet (not shown) as well as to aspirate gastric fluids through the nasoesophageal catheter or feeding tube.

FIG. 2 discloses one embodiment of esophageal pH monitor 10 in which esophageal conduit 16 includes a nasoesophageal catheter. Examples of preferred nasoesophageal catheters include polyethlyene enteral feeding tubes such as that disclosed in U.S. Pat. No. 3,058,472 having an outer diameter of 2.67 ml. or a polyurethane nasoesophageal feeding tube having an outer diamter of 2.7 ml. such as the Travasorb ™ tube (Travenol Laboratories). A nasoesophageal catheter is preferred as conduit 16 to permit usage of a removable wire stylet for intubation purposes. FIG. 2 also discloses nasoesophageal catheter 16 as including outlet openings 16d which permit aspiration of fluid through outlet 16d by means of a syringe (not shown) or other suction device seated within luer end 16c.

FIG. 3 discloses one embodiment of indicator envelopes 12 and 14. Envelopes 12 and 14 preferably are comprised of a semi-permeable membrane such as cellophane dialysis membrane. A suitable semi-permeable dialysis membrane is Semi-Micro ™ (Spectrum Medical Industries, Inc.) having an outer diameter of 2.5 ml. The embodiment of envelopes 12 and 14 disclosed in FIG. 3 is secured to esophageal conduit 16 by strands of ligature 18, preferably surgical silk tie, in which ligature 18 is coated with and adhered to conduit 16 through use of a non-toxic adhesive such as silicone rubber cement.

FIG. 4 discloses another embodiment of indicator envelopes 12 and 14 in which envelope 12' includes a removable semi-permeable sleeve which surrounds the outer diameter of conduit 16. Envelope 12' is maintained in a selected stationary position along conduit 16 by means of retaining collars 20.

FIG. 5 discloses the manner in which envelope 12' or 14' seats about the outer diameter of esophageal conduit 16 and the manner in which envelope 12' contains an ion exchange color indicator composition which is utilized to determine on a semi-quantitative basis the length of time in which the indicator envelopes have been exposed to a clinically significant pH.

The ion exchange color indicator composition utilized in monitor 10 is comprised of a weak cation exchange substance in combination with a bound non-toxic dye. The weak cation exchange substance may be either a resin, a cellulose or an agarose composition. Exemplary resins include Bio-Rex 70 (Bio Rad), IRC-50 (Rohm & Haas) and C-464 (Diamond Shamrock). Exemplary celluloses include Cellex CM (Bio Rad) and CM-Sephadex (Pharmacia Fine Chemicals). Exemplary agaroses include CM Bio Gel A (Bio Rad) and CM-Sepharose (Pharmacia Fine Chemicals). A preferred ion exchange substance must be non-toxic, sterilizable, have a long shelf life and must be a weak cation exchanger with a preferred pK of from 4 to 5.

Ion exchange substances which are weak cation exchangers are typically carboxylic acids of the form R—COO— or R—O—CH2—COO—. In the case of a cation exchange substance comprising a resin, R would denote a macroreticular acrylic polymer lattice. R would likewise denote the glucose polymer units characterizing cellulose and the galactose polymer units characterizing agarose. The function of the negatively charged sites on the preferred cation exchange substances is to attract free positively charged hydronium ions from the acidic gastric fluid through the semi-permeable membrane of the indicator envelope and binding such hydronium ion to displace indicator dye. pK commonly describes the pH at which one half of these reactive species are ionized, e.g. R—COO—, and one half are neutral, e.g. R—COONa or R—COOH. The preferred weak cation exchange substances of the present composition should have a pK of from 4 or 5 in order to be most neutralized at a clinically significant pH. For example, if the cation exchange substance has a pK of 5, then at pH 7, 99% of reactive sites would be charged and 1% would be neutral. At pH 6, 90% of sites would be charged and 10% would be neutral. At pH 5, 50% of reactive sites would be charged and 50% would be neutral. At pH 4, 10% of sites would be charged and 90% would be neutral. At pH 3 and below, less than 1% of sites would be charged and greater than 99% would be neutral. Generally, an ion exchange substance is "neutralized" at a pH of 2 or more units below its pK, since at a pH below this, less than 1% of reactive sites are charged and capable of binding ions.

The preferred cation exchange substance in the present invention should be substantially neutralized at an esophageal pH which is clinically significant, i.e. at pH 4 or less. Thus, during those times of clinically significant gastroesophageal reflux, the cation exchange substance is neutralized so that the dye diffuses out of the ion exchange color indicator composition and becomes flushed into the gastrointestinal tract. For example, if the specific dye were bound to an cation exchange substance with pK 5, then when esophageal pH were 7, very little dye would be eluted. When esophageal pH drops to 6, then 10% of the binding sites would be neutralized, and the dye would slowly release and diffuse from the cation exchange substance. At pH 5, moderate diffusion would occur, since 50% of binding sites would be neutralized. At a clinically significant pH of 4, 90% of sites would be neutralized and rapid diffusion of dye would occur. At a pH of 3 and below, essentially all binding sites would be neutralized and diffusion of dye would be limited only by the diffusion characteristics of the cation exchange substance.

The cation exchange substance is intermixed and loaded with a non-toxic, cationic indicator dye preferably either methylene blue or azure A. Upon intubation of monitor 10, the initial coloration of indicator envelope 12 is a deep blue/purple due to the presence of the indicator dye in the ion exchange color indicator composition. When exposed to esophageal gastric acid, free hydronium ions present in gastric fluid pass through the semi-permeable membrane comprising envelopes 12 and 14. Upon passage into envelopes 12 and 14, the hydronium ions become attracted to and bind on the charged sites of the cation exchange substance and displace the indicator dye from the cation exchange substance.

FIG. 6 discloses the preferred performance of the preferred ion exchange color indicator composition having a pK of from 4 through 5 in which the percent of indicator dye remaining bound to the weak cation exchange substance is plotted against time and decreasing ambient pH. The degree of discoloration (or percentage of dye remaining bound to the cation exchange substance) indicates the total length of time during which envelope 12 and 14 have been exposed to low ambient pH conditions. It should be understood that esophageal pH monitor 10 of the present invention does not function strictly as a prior art acid-base indicator. Rather monitor 10 quantitates the duration of exposure of ion exchange color indicator composition to a low ambient pH. The is in contradistinction to the prior art devices discussed above which merely measure the pH at a site within the gastrointestinal tract at a single instant in time.

FIG. 6 discloses that the disassociation of the cationic indicator dye from the weak cation exchange substance is both a function of time and pH. At a given pH, the loss of dye is linear. With decreasing pH the rate of loss of dye bound to the ion exchange substance increases, but remains linear with time. It has been determined that a cation exchange substance having a pK of between 4 through 5 will become substantially discolorized at a clinically significant pH of 4 or less, e.g. at pH 4 10% of the indicator dye remains bound to the cation exchange substance. During periods of clinically significant reflux, dye is rapidly eluted from the ion exchange color indicator composition.

Figure 7:
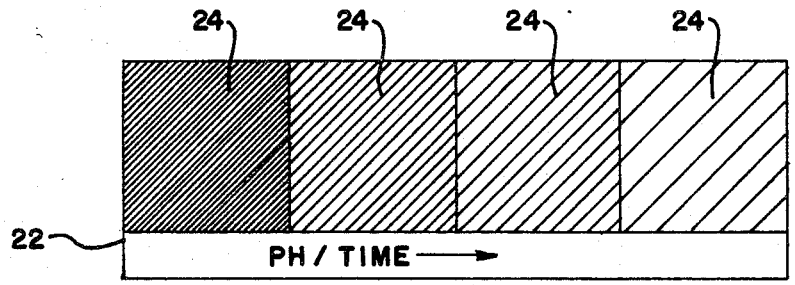

The total length of time of clinically significant reflux resulting in abnormally low pH may be ascertained by colorimetric analysis. For example, the discolorized indicator envelope 12 may be visually compared against a colormetric analysis rule 22 disclosed in FIG. 7. A continuum of color panels 24 contained on rule 22 are developed by in vitro experimentation establishing the degree of discolorization of the ion exchange color indicator composition as a function of time and pH. Of course, it is within the scope of the present invention that colormetric analysis of the discolorized indicator envelope 12 may also be conducted on an appropriate colorimetric instrument.

The esophageal pH monitor of the present invention may also be understood with reference to the following example:

EXAMPLE

Dialysis tubing, about 3-5 cm in length is filled with a weak cation exchange substance, for example, CM-Sepharose, having a pK of between 4 and 5. The tubing is then ligated at both ends creating a sealed envelope. The envelope is dialyzed at room temperature in three liters of phosphate buffered tap water (NaH2PO4/Na2HPO4, 300 mOsm/l) at pH 6.3 for 4 hours. The envelope is then placed in 100 ml of the same solution to which is added methylene blue, 0.01%, and allowed to equilibrate for 20 hours with gentle stirring. The envelope containing the activated ion exchange color indicator composition is placed in 3 liters of phosphate buffered tap water as described and dialyzed for 24 hours at room temperature. The 24 hour dialysis is repeated one time. This procedure loads the binding sites of the cation exchange substance with methylene blue and washes out all unbound dye.

Strands of ligature, such as surgical silk, are cemented near the distal end of the nasojejunal feeding conduit and again at approximately 3-5 cm to the first ligature. The envelope containing the methylene blue treated cation exchange substance is tied to the distal end of a nasojejunal feeding conduit with the previously cemented ties. A second envelope as a control may also be ligated about 25 cm from the first envelope. The conduit is intubated orally or nasally to a predetermined length. After a predetermined time period, the conduit is removed and the degree of coloration of the indicator envelope is visually compared to a color rule indicating the length of time of exposure to low pH.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. For example, an anion exchange resin bound to a non-toxic anionic dye may be placed within an envelope situated in the stomach to semi-quantitatively determine the amount of time of exposure to ambient pH of 7 or greater. Therefore, it is intended that the invention not be limited to a particular embodiment disclosed as the best mode contemplated for carrying out the invention, but that the invention will include all embodiments falling within the scope of the appended claims.

I claim:

1. A self-contained diagnostic pH monitor for preliminary screening of gastroesophageal reflux disease and suitable for esophageal intubation without restriction of patient movement and activity, the monitor determining duration of exposure to pH levels clinically significant for gastroesophageal reflux disease, the monitor omitting use of external power, light and data processing sources, comprising:
   a nasoesophageal probe for selected esophageal intubation, the probe having a length permitting positioning of a distal end of the probe proximal to the gastroesophageal junction of the esophagus;
   at least one semipermeable envelope, the envelope being carried near the distal end of the probe, the envelope containing a composition including a cation exchange substance having an ionic dye bound thereto, the envelope being constructed of a material permeable to both hydronium ions and the ionic dye;
   said composition substantially and irreversibly discoloring in response to extended exposure to a pH of 4 or less and upon withdrawal of the probe the composition in said envelope being colorimetrically analyzable to semi-quantitatively determine the duration of exposure to pH levels being clinically significant for preliminary screening of gastroesophageal reflux disease.

2. The pH monitor of claim 1 wherein the cationic exchange substance has a pK of at least 4.

3. The pH monitor of claim 2 wherein the cationic exchange substance has a pK of between 4 and 5.

4. The pH monitor of claim 1 wherein the cationic exchange substance is selected from the group consisting of a resin, a cellulose and an agarose.

5. The pH monitor of claim 1 wherein the ionic dye is selected from the group consisting of methylene blue and azure A.

6. The pH monitor of claim 1 further including a second semi-permeable envelope carried proximal to the one semi-permeable envelope, said second semi-permeable envelope being generally intermediately positioned along the probe.

7. The pH monitor of claim 1 wherein the probe includes a nasoesophageal catheter.

* * * * *